United States Patent [19]

Numata et al.

[11] Patent Number: 4,898,462

[45] Date of Patent: Feb. 6, 1990

[54] DEVICE FOR DETECTING A TRANSMISSIVITY OF A SUBSTANCE

[75] Inventors: Koji Numata; Fumio Asakura, both of Toyohashi; Yoshiyuki Kago, Nishio; Masaei Nozawa, Okazaki; Takahiro Shibakawa, Kariya; Hajime Akado, Anjyo; Hideharu Kato, Nukata, all of Japan

[73] Assignees: Nippondenso Co., Ltd., Kariya; Nippon Soken, Inc., Nishio, both of Japan

[21] Appl. No.: 160,302

[22] Filed: Feb. 25, 1988

[30] Foreign Application Priority Data

Feb. 26, 1987 [JP] Japan .................. 62-43967
Mar. 5, 1987 [JP] Japan .................. 62-51153

[51] Int. Cl.$^4$ .................. G01N 33/28; G01N 21/59
[52] U.S. Cl. .................. 356/70; 250/573; 331/66; 356/436; 356/442
[58] Field of Search .................. 356/70, 436, 437, 442, 356/250; 250/573; 350/536; 331/66

[56] References Cited

U.S. PATENT DOCUMENTS

| 1,480,391 | 1/1924 | Hausser | 350/536 |
|---|---|---|---|
| 3,334,309 | 8/1967 | Murphy et al. | 331/66 |
| 3,671,751 | 6/1972 | Kortge et al. | 331/66 |
| 3,933,046 | 1/1976 | Ebrecht | 331/66 |
| 4,003,661 | 1/1977 | Yamano | 356/436 |
| 4,622,465 | 11/1986 | Harig et al. | 356/70 X |
| 4,699,509 | 10/1987 | Kamiya et al. | 356/70 |
| 4,725,148 | 2/1988 | Endo et al. | 356/432 |

FOREIGN PATENT DOCUMENTS

| 57-98842 | 6/1982 | Japan . | |
|---|---|---|---|
| 60-59142 | 4/1985 | Japan . | |
| 60-92156 | 6/1985 | Japan . | |
| 60-105962 | 6/1985 | Japan . | |
| 60-131615 | 9/1985 | Japan . | |
| 60-259935 | 12/1985 | Japan | 356/442 |
| 61-10912 | 1/1986 | Japan . | |
| 61-57842 | 4/1986 | Japan . | |
| 61-44413 | 10/1986 | Japan . | |

OTHER PUBLICATIONS

English Abstract of Japan 61-44413 published 3/1986.
English Abstract of Japan 60-105962 published 6/1985.
Partial English translation of Japan UM (Unexamined) 61-57842.

*Primary Examiner*—Vincent P. McGraw
*Attorney, Agent, or Firm*—Cushman, Darby & Cushman

[57] ABSTRACT

A device for detecting a transmissivity of a substance utilizing a transmitted light value, which comprises a light emitting element and a photo detecting element. The light emitting element and the photo detecting element are spaced from each other at a predetermined distance so that a transmitted light value of a substance passing through the space is detected as an amount of light transmitted therethrough. The photo detecting element further comprises a photo oscillator circuit including the photo detecting element as one component thereof and outputs a signal having characteristics selected from a cycle and a frequency corresponding to the transmitted light value, and when the condition of a substance exceeds a predetermined reference level, such information is displayed at a display unit. Further, the device carries out a detecting and discriminating operation when a temperature of a substance is at a level lower than a maximum temperature at which each component of the detecting circuit will not work effectively.

The device is also provided with a detecting unit in which the light emitting element and the photo detecting element are kept firmly in contact with each other, with a spacer placed therebetween, by an external force caused by a spring, to make the space provided therebetween constant regardless of any deformation of any component of the device caused by heat or aging.

13 Claims, 11 Drawing Sheets

| Fig.10A | Fig.10B | Fig.10C |

DEVICE FOR DETECTING A TRANSMISSIVITY OF A SUBSTANCE

BACKGROUND OF THE INVENTION

1. Field of the Invention

The present invention relates to a device for detecting a transmissivity of a substance by utilizing a transmitted light value, and more specifically, relates to a device for detecting a degree of contamination of a fluid, for example, a gas or a liquid.

2. Description of the Related Art

In many industrial fields a check of the transmissivity of a substance is made, during and after manufacture, and further, upon use thereof, by using a transmitted light value.

For example, when mixing a plurality of substances such as gases or liquids to produce a different substance, or when blending certain ingredients, for example, inorganic particles such as carbon, ferrite, antimony oxide or dyestuff into a base material such as water, paste or resin, a continuous check of the transmissivity of each material used or produced in the respective process must be made by using a detecting system utilizing a transmitted light value system, to ensure that the product has a predetermined condition, including the quality or contamination thereof, or to maintain the processing conditions at the optimum state.

Further, a level of contamination of a substance such as a gas or liquid used in a certain process must be checked to carry out a process control, or to determine when the substance must be discharged before causing environmental pollution. For example, a degree of contamination of a lubricating oil of an internal combustion engine by carbon particles contained therein must be checked.

Generally speaking, a check of a transmissivity of a substance, i.e., the quality or contamination thereof, is made by using a transmitted light value, which is represented by a ratio of an intensity of an incident light to an intensity of a transmitted light when a light is incident on a substance such as a liquid or a gas having particles therein. This light transmittance is defined by the following equation.

$$\alpha = 1/l \times ln\, I_0/I$$

Wherein, $\alpha$ represents a light transmittance which relates to a function representing a condition including a quality or level of contamination of a substance, $l$ represents a thickness of an article, and $I_0$ and $I$ represent an intensity of an incident light and an intensity of a transmitted light, respectively.

Therefore, by arranging a light emitting element and a photo detecting element at a predetermined space therebetween, and placing a substance to be checked in that space, a light transmittance value depending upon a condition of the substance can be obtained from the output of the photo detecting element.

However, in the light transmittance representing a certain condition of a substance by such a detecting system, as apparent from the equation above, the output of the photo detecting element becomes extremely low because the strength of the transmitted light is logarithmically reduced as the degree of contamination is increased.

Accordingly, problems arise in that it is difficult to transmit such a weak output signal to a display means provided, for example, at a location remote from the detecting device, and thus the transmitted signal must be amplified, which means that an amplifier capable of a large amplification must be provided in the vicinity of the photo detecting element.

Further, other problems arise in this type of detecting system, such as another circuit, for example, a comparator for comparing the transmitted light with the incident light or a compensating circuit for compensating for variations in the amount of light emitted from the light emitting element, must be provided, thus increasing the size of the detector system and making the configuration thereof more complex.

Also, as discussed hereafter, another problem will arise when such a system is used for detecting a degree of contamination of a lubricating oil of an internal combustion engine, for example, a diesel engine. In this system, a degree of contamination of the lubricating oil by carbon particles is usually measured.

Generally speaking, a lubricating oil of an internal combustion engine should be changed periodically to avoid an increase of the wear of slidable parts of the engine caused by contaminated oil.

The amount of contamination of the lubricating oil differs significantly in accordance with the operating conditions of the engine, but the periods at which the lubricating oil changed are usually based on the length of time for which the engine has been operated or the distance that the vehicle has been driven.

Accordingly, problems arise in that the lubricating oil is wasted by changing it too early or wear of the sliding portions of the engine is greatly increased because the oil is not changed before the degree of contamination thereof becomes too high.

In a diesel internal combustion engine in particular, a large number of carbon particles contained in the exhaust gas are mixed in the lubricating oil, and therefore, the problems mentioned above become more important because the lubricating oil is contaminated in a relatively short time when compared with an internal combustion engine using gasoline.

To overcome these problems, Japanese Unexamined Patent Publication 57-98842 disclosed a system in which a degree of contamination is detected by detecting a degree of a transparency of the lubricating oil when placed in the space between the light emitting element and the photo detecting element, both of which are immersed in the lubricating oil, and a display lamp is turned ON when a signal is output at a certain degree of contamination of the lubricating oil, to signify that the oil must be changed.

But if such a system is used to detect a degree of contamination value of a lubricating oil in a diesel internal combustion engine, for example, since the light emitting element and photo detecting element must be immersed in the lubricating oil, the temperature of which becomes as high as 145° C., the light emitting element and the photo detecting element must be able to operate at such a high temperature, and such elements having a high heat resistance are not easily obtained commercially.

In experiments with a diesel internal combustion engine using a light emitting diode (LED) as a light emitting element and a silicone photo diode (SPD) as a photo detecting element, it was found that the output current of said photo detecting element was extremely low, i.e., a micro current of about 1 nA, and because of the very low output current, it was necessary to provide an amplifier or the like near the photo detecting element. However, difficulties arose in the operation of such an amplifier at a temperature as high as 145° C.

SUMMARY OF THE INVENTION

In order to overcome the problems described above, the present invention provides a detecting device for detecting a transmissivity of a substance, including a quality or degree of contamination of the substance by utilizing a transmitted light value obtained by a device which can develop a strong output signal corresponding to a condition of a substance the device having a simple circuit and not using an amplifier or comparator, and further, the present invention provides a device for detecting a transmissivity of a substance, including a degree of contamination of a fluid, wherein a light emitting element and a photo detecting element are protected from heat even when a temperature of a substance, for example, a gas or fluid, is very high.

Therefore an object of the present invention is to provide a detecting device for detecting a transmissivity of a substance, by which a strong output signal corresponding to the condition of a substance is developed; the device having a simple circuit and not using an amplifier.

It is also an object of the present invention to provide a device for detecting a transmissivity of a substance, including a degree of contamination of a fluid, in which a light emitting element and a photo detecting element are protected from heat even when a temperature of a substance, for example, a gas or fluid, is very high.

Another object of the present invention is to provide a device for detecting a transmissivity of a substance, which is not effected by changes in a temperature and thus can maintain an accurate and precise operation even in high temperature environment, and further, can transmit an output signal to a display means remote from the detector without interference by noise.

Another object of the present invention is to provide a device for accurately detecting a transmissivity of a substance by maintaining a constant space between the light emitting element and the photo detecting means even when one of those components is deformed by a change of temperature or by aging.

A further object of the present invention is to provide a device for detecting a transmissivity of a substance, in which a photo detecting element can effectively receive a large amount of the light emitted from the light emitting element.

Another object of the present invention is to provide a device for detecting a transmissivity of a substance with a greater accuracy by defining a distance between the space the light emitting element and the photo detecting means as a distance which a substance, for example, a fluid, to be detected can be passed therebetween but less than a maximum range of the light emitted across that space.

To attain the objects of the present invention, a device for detecting a transmissivity of a substance, in accordance with the invention, comprises a light emitting means including a light emitting element and a photo detecting means including a photo detecting element. The light emitting means and the photo detecting means are spaced from each other at a predetermined distance so that a transmitted light value of a substance passing through that space is detected as an amount of light transmitted therethrough, wherein the photo detecting means comprises a photo oscillator circuit including the photo detecting element as one component element thereof and outputting a signal having characteristics selected from a certain cycle and a certain frequency corresponding to the transmitted light value. The photooscillator circuit is incorporated with the photodetecting element as a unit in the housing portion.

Further, a device for detecting a transmissivity of an article, especially a degree of contamination of a fluid, provided in accordance with this invention comprises, a detecting means having a light emitting means and a photo detecting means, both of which are immersed in a fluid to detect the amount of the light emitted from the light emitting means by the photo detecting means through the fluid material, a discriminating means for discriminating a level of a transmissivity of the substance based upon the signal output from the detecting means, and an electric power control means for cutting off a supply of electric power to the detector when the temperature of detecting device is higher than a predetermined temperature.

DESCRIPTION OF THE PREFERRED EMBODIMENTS

The preferred embodiments of the present invention will now be described with reference to the accompanying drawings. Note, the embodiments will be described mainly with reference to a device used for detecting a degree of contamination of a liquid.

Also note, this invention is not restricted to the device described hereunder as one embodiment but further includes the protection of devices used in any field mentioned above, after necessary and obvious modification.

Embodiments of this invention of a detecting device for detecting a transmissivity of a substance will be described with reference to the drawings.

Figure 1:
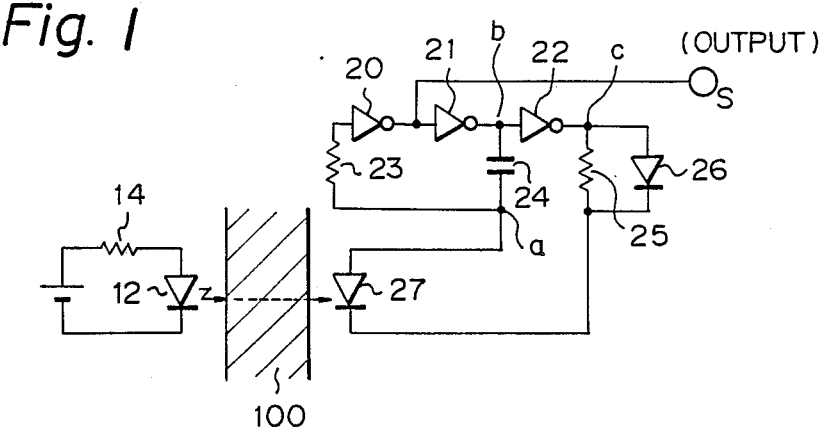
FIG. 1 shows an electric circuit of one embodiment of a detecting device of the invention.

FIG. 1 shows a basic concept of an electric circuit of one embodiment of the detecting device of this invention, having a light emitting element and a photo detecting element.

In FIG. 1, a light emitting diode (LED) 12 is used as a light emitting element, and the circuit is provided with a resistor 14 for controlling a current of the light emitting diode (LED) 12.

CMOS inverters 21, 22, and 2 (e.g., TOSHIBA TC 4069UBP) consisting of an astable multivibrator with a current controlling resistor 23, a timing condenser 24, and a timing resistor 25 are provided, and a diode 26 is coupled in parallel to the timing resistor 25.

A photo detecting element 27 consists of an SPD (Silicone Photo Diode) and is series-connected to the timing condenser 24 and the timing resistor 25, and an output S of this photo detecting element 27 is taken out from the inverter 20.

In this embodiment, a light emitting diode (LED) 12 and a photo detecting element 27 (SPD) are arranged face to face with a micro space therebetween and immersed in a lubricating oil 100 of a diesel internal combustion engine.

These elements 20 to 26 are arranged in such a way that a total connecting line provided among these elements is kept as short as possible.

The operation of the circuit described above will now be explained.

Figure 2:
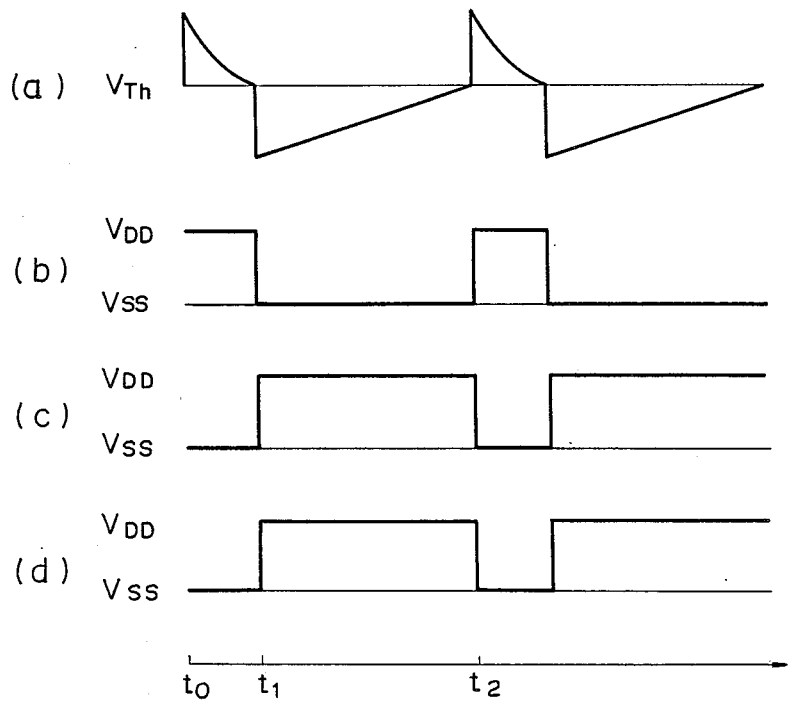
FIG. 2 shows waveforms at each point of the circuit in FIG. 1.

FIG. 2 shows the voltage waveforms output from each point in FIG. 1.

First, assuming that, when the output of the inverter 20 is low level (hereinafter referred to as "L" level) at a time $t_0$, the output of the inverter 21 at point b and the output of the inverter 22 at point c are high level (hereinafter referred to as "H" level) as shown in FIG. 2(b) and "L" as shown in FIG. 2(c), respectively, and therefore, the voltage output at point a in FIG. 2(a) is brought down exponentially by a current from the timing condenser 24 to the timing resistor 25 through the SPD 27 with a time constant determined by a value of the timing condenser 24 $C_T$ and a value of the timing resistor 25$R_T$.

At a time $t_1$, when the voltage at point a falls below the threshold input voltage $V_{TH}$ of the inverter 20, the output of each inverter 20, 21, and 22 is reversed, respectively, and thus the voltage at point a falls to the level of $V_{TH}-V_{DD}$ ($V_{DD}$ is the power supply voltage).

During the time from time $t_1$ to time $t_2$, the voltage at point a is increased gradually by a current developed by the SPD 27 in proportion to an amount of a light value detected by the SPD 27 from the diode 26 to the timing condenser 24, because the SPD 27 has a reverse bias.

Assuming that the diode 26 is not provided in the circuit, a current would flow from the timing resistor 25 to the timing condenser 24 through SPD 27, but as long as the current developed by the SPD 27 depending upon the amount of a light value detected thereby is large, the current proportional to an amount of a transmitted light value detected by the SPD 27 does not flow in the circuit because, under such a situation, a voltage drop at the timing resistor 25 occurs and thus a forward voltage is applied to the SPD 27.

When the voltage at point a reaches the threshold voltage $V_{TH}$ at the time $t_2$, the output of each inverter 20, 21, and 22 is again reversed, respectively, and thus the voltage at point a is raised to the level of $V_{TH}+V_{DD}$.

Therefore, an oscillation is developed and the output S as shown in FIG. 2(d) is taken out, but the cycle from time $t_0$ to time $t_1$ is determined by a value of the timing condensor 24$C_T$ and a value of the timing resistor 25$C_T$.

The cycle from time $t_1$ to time $t_2$ is proportional to an amount of a light value detected by the SPD 27, because it is determined by a value of the timing condenser 24 and the current proportional to an amount of a transmitted light value detected by the SPD 27.

On the other hand, the amount of the transmitted light value detected by SPD 27 corresponds to a light from the LED 10, which is transmitted through a lubricating oil, and thus the following equation stands.

$$\alpha' = A + B \times \ln T_2$$

Wherein $T_2$ represents a cycle from $t_1$ to $t_2$, $\alpha'$ represents a transmitted light value and a degree of contamination of, for example, the oil, and A and B are constant.

Figure 3:
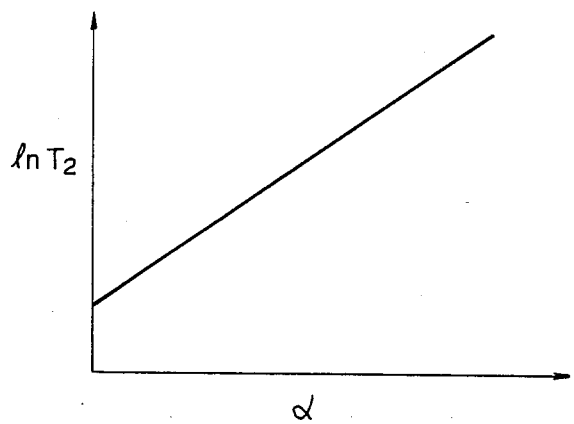
FIG. 3 is a characteristic chart showing a relationship between a transmitted light value $\alpha'$ and a cycle of the output signal of the photo oscillating circuit in the embodiment of FIG. 1.

The characteristic chart using this equation is shown in FIG. 3.

As described above, if a degree of contamination of, for example, an oil, is an intended condition to be detected, first a transmitted light value is detected by a light detecting sensor mentioned above and the detected transmitted light value is then converted into an oscillating signal having a cycle corresponding to the detected light value which corresponds to a degree of contamination.

Next, a circuit for discriminating a degree of contamination for example, in such a way that it is determined whether or not the transmitted light value detected exceeds a predetermined value, will be explained hereunder.

Figure 4:
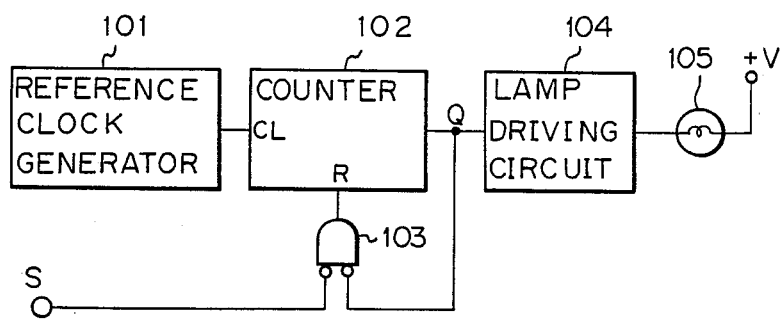
FIG. 4 is a diagram of a discriminating and display circuit for a contamination level used in the embodiment of FIG. 1.

FIG. 4 is a schematic diagram of a circuit for discriminating a degree of contamination using a signal representing the transmitted light value, and sending the resultant output to a display means, which comprises a reference clock generator 101, a counter 102, an AND gate 103, a lamp driving means 104, and a lamp 105.

In FIG. 4, a signal S as shown in FIG. 1 having a cycle $T_2$ corresponding to the amount of the transmitted light value is input to a reset terminal R of the counter 102 through the AND gate 103, and the reference clock signal output from the reference clock generator 101 is input to a clock terminal CL of the counter 102.

A large transmitted light value means a degree of contamination is low, and thus an output Q of the counter 102 is maintained at the "L" level because a reset signal having an "H" level is input to the counter 102 at short intervals.

Conversely, when the transmitted light value becomes small, i.e., the degree of contamination becomes higher than a predetermined level, the interval of the input signal input to the reset terminal is lengthened, and therefore, the counter counts up a predetermined number Q is made "H" level.

This "H" level output Q is input to one input terminal of the gate 103 and the reset of the counter 102 by the cycle signal S is prevented, and thus the output Q remains at the "H" level.

The output Q then causes the lamp driving means 104 to turn the lamp 105 ON. Namely, when the degree of contamination of the lubricating oil is increased, the lamp 105 is turned ON.

Figure 5:
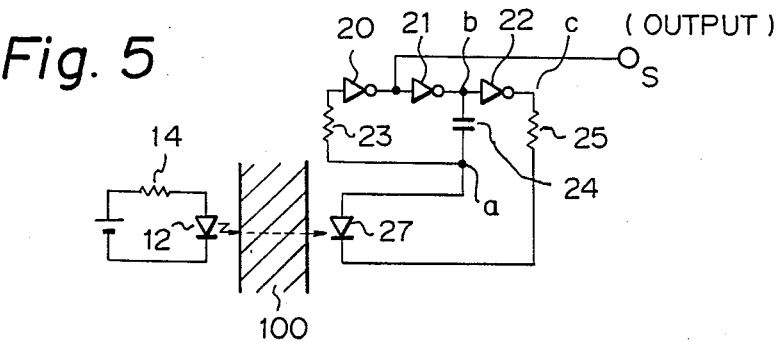
FIG. 5 shows an electric circuit of the second embodiment of the invention.

The second embodiment of this invention will now be described with reference to FIG. 5.

Figure 6:
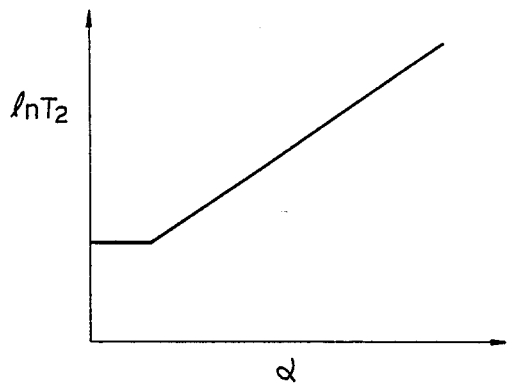
FIG. 6 is a characteristic chart showing a relationship between a transmitted light value and a cycle of the second embodiment in FIG. 5.

In this embodiment, a diode 26 is omitted from the circuit shown in FIG. 1 and therefore, the characteristic of this circuit shows a configuration such as shown in FIG. 6 in that, when a degree of contamination is low, i.e., in the range in which the amount of the transmitted light value detected by the photo detecting element is large, the cycle $T_2$ is not reduced and becomes saturated.

Accordingly, the device of this embodiment is a suitable for detecting a degree of contamination beyond a predetermined level.

Figure 7:
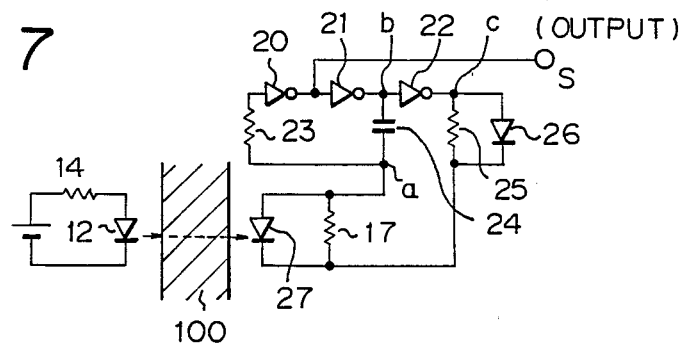
FIG. 7 shows an electric circuit of the third embodiment of the invention.

The third embodiment of this invention will be described with reference to FIG. 7.

Figure 8:
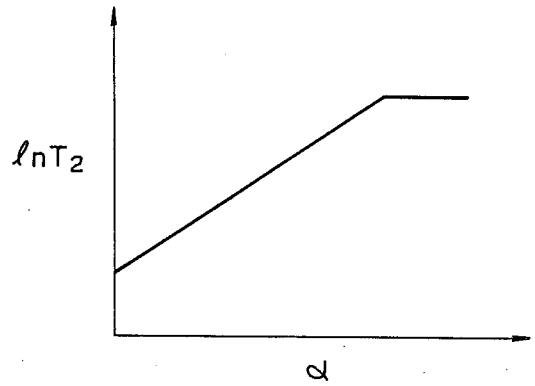
FIG. 8 is a characteristic chart showing a relationship between a transmitted light value and a cycle of the third embodiment in FIG. 7.

In this embodiment, a resistor 17 connected in parallel to the SPD 27 is added to the circuit shown in FIG. 1, and therefore, the characteristic of this circuit shows a configuration such as shown in FIG. 8 in that, when a degree of contamination reaches a certain level above a predetermined value, the cycle $T_2$ is not increased and becomes saturated.

This means that, when a degree of contamination is high, then the length of the cycle $T_2$ is logarithmically greatly increased, and therefore, the device of this embodiment is suitable for detecting a degree of contamination when problems arise because the cycle $T_2$ is too long.

In this embodiment, the resistor 17 can be replaced by a reversed diode used as a high resistance.

Figure 9:
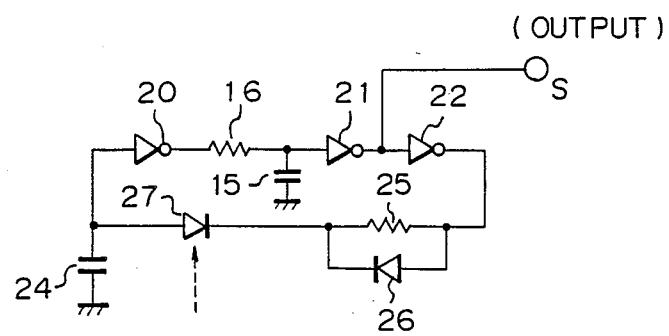
FIG. 9 shows an electric circuit of the fourth embodiment of the invention.

The fourth embodiment of this invention will now be described with reference to FIG. 9.

This embodiment shows another example of a photo oscillating circuit in which an oscillating cycle is varied in accordance with a current developed by the SPD 27 caused by the detected light, and which comprises the resistors 25 and 16, the condensers 24 and 15, the inverters 20, 21, and 22, and the diode 26, in addition to the SPD 27, and an output S is taken out from the inverter 21.

Further, in this invention, a warning lamp is turned ON when the degree of contamination exceeds a predetermined value. Such a degree of contamination can be detected as a voltage proportional to the degree of contamination by utilizing a Frequency-Voltage converter or the like, and that value may be displayed on a suitable meter or may be displayed in digital form.

Next, a detecting device in accordance with this invention will be further described.

The basic construction of the detecting device, as mentioned above, comprises a light emitting element and a photo detecting element arranged face to face with a space therebetween. These elements are incorporated into a unit, a basic configuration thereof being shown in FIG. 11 as one embodiment, but a problem remains of a distance between the light emitting element and the photo detecting element.

That is, heretofore, many proposals have been made for measuring a degree of contamination of, for example, a lubricating oil, by utilizing a light transmitted from a light emitting element and detected by a photo detecting element, as shown for example, in Japanese Unexamined Utility Patent Publication Nos. 60-131615, 60-59142, 60-92156 and 61-10912.

However, it is important to maintain a constant distance between these elements when detecting a condition of a substance by using a transmitted light value or a light transmittance or the like, but these prior arts do not disclose a means for fixing this distance at a predetermined length and thus this distance is easily varied by deformation of an element used in the device by a mechanical force or a change in thermal conditions, for example.

According to this invention, this problem is overcome by constituting the device as follows.

Namely, in this invention, a device for detecting a transmissivity of a substance comprises a cover having at least one opening for a material to be passed therethrough, a light emitting element and a photo detecting element provided inside of the cover and spaced at a predetermined length from each other with a spacer provided therebetween, this space matching the opening of the cover, at least one housing provided inside the cover to support the light emitting element and the photo detecting element, and a spring provided inside the cover to ensure a firm contact between the light emitting element and the photo detecting element.

Figure 13:
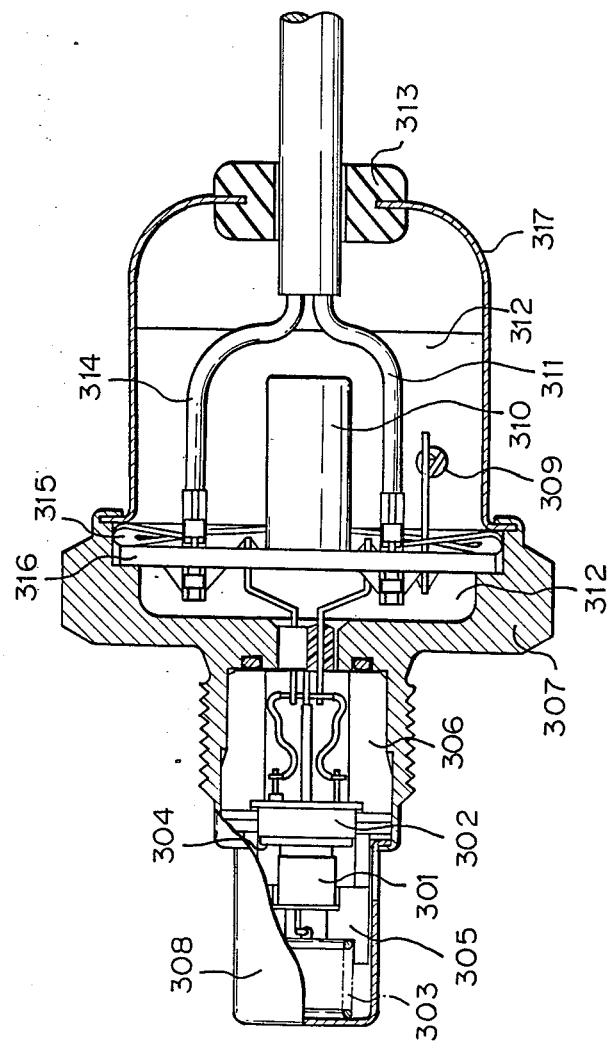
FIG. 13 is a cross sectional view of an entire detecting device used in this invention.

According to this invention, the space between those elements can be firmly fixed at a predetermined length by utilizing a spacer and a spring, even when a deformation of any of the parts comprising the device occurs because of a variation of a temperature, aging of the parts, or a mechanical force. As shown in FIG. 13, the device comprises a light emitting means 301 including a light emitting element, a photodetecting means 302 including a photo-detecting element and photooscillating circuit in the form of a unit coil spring 303, a spacer 304, housings 305 and 306, both made of a plastic, a housing 307 made of a metal, and a cover 308 made of a metal.

According to this invention as described above, the device is characterized in that the space between the elements is kept constant by placing a spacer between the elements and a spring between a housing and a cover, and further, by applying a calking force of a housing 307 first to a cover 308, and thereafter, transmitting the force to a spring 303, a housing 305, a light emitting element 301, a spacer 304, and a photo detecting means 302, in turn.

The cover of this embodiment has at least one opening for a substance to be passed therethrough, at a portion in the vicinity of the light emitting element and the photo detecting element.

As shown in FIG. 13, the main portion of the device of the invention is further connected to a transmission line by a suitable coupling means. Such a configuration is illustrated in the FIG. 13 as one embodiment, and comprises a printed circuit board 316 connected to the housing 307 with a plate spring 315 which biases the printed circuit board 316 against the housing 307, and an IC oscillating circuit 310, a resistor 309, which controls a resistance of the circuit to adjust a value of an emitted light, an input harness 311, and an output harness 314 are mounted on the board 316.

These components are covered by a cover 317 made of a metal with moisture-proof silicone filler 312 filled inside thereof, and both harnesses are led out through an aperture thereof having a grommet 313 made of a rubber provided thereon.

In this invention, the distance of the space is very important and should be determined while taking a characteristic of a substance to be detected and a performance of a light emitting element and a photo detecting element into consideration.

In this embodiment, in which a lubricating oil of an internal combustion engine containing carbon particles is used, the distance thereof is preferably from 40 μm to 170 μm and the minimum value is determined as the width through which a substance to be detected, for example, a lubricating oil of an internal combustion engine containing carbon particles, can pass, and the maximum value is determined as a maximum distance over which the light for detecting a degree of contamination can be transmitted.

Figure 17:
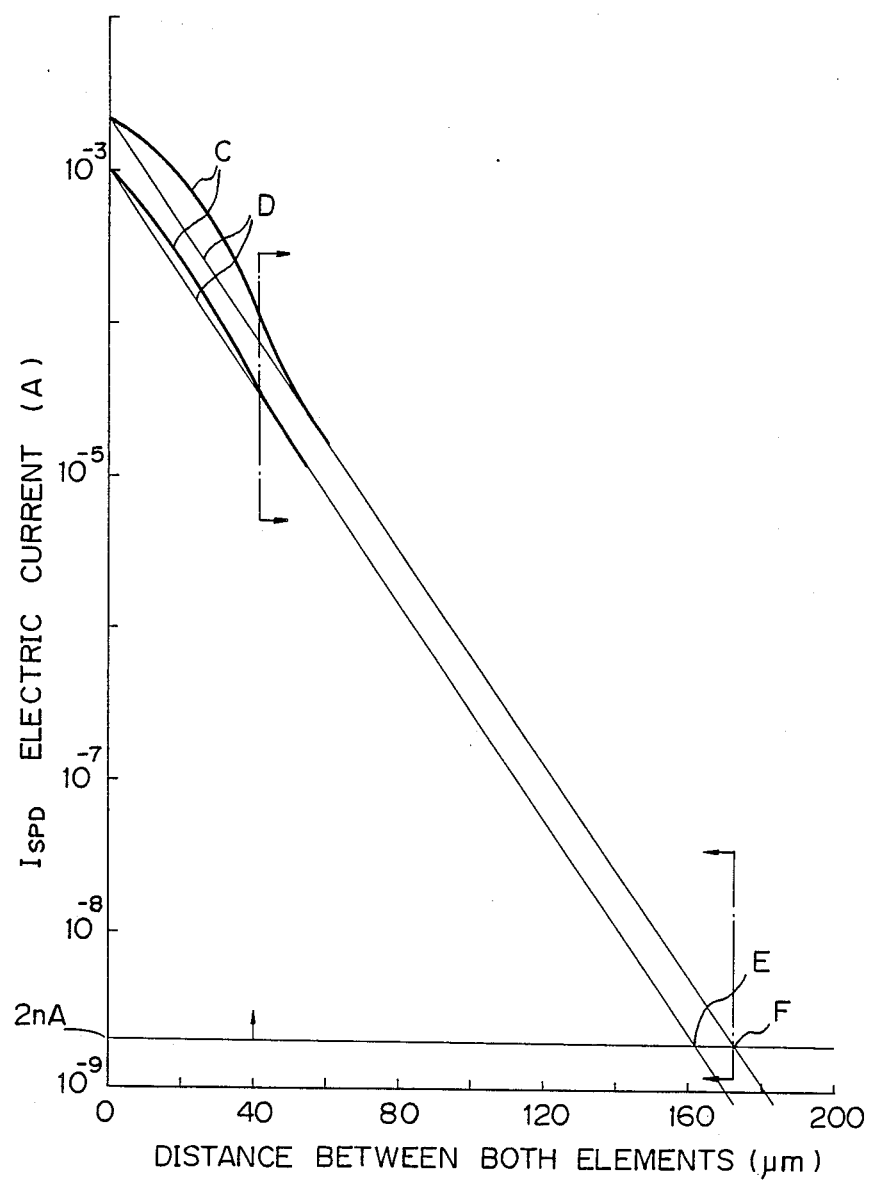

FIG. 17 shows a relationship between a distance of a space provided between the light emitting element and photo detecting element and a current generated by a photo detecting element corresponding to a detected light transmitted through a substance.

Here, a lubricating oil containing 3% by weight of carbon particles is used when detecting a transmitted light value at a temperature of 23° C., and an electric current corresponding to the transmitted light value is shown in relation to a distance of the space.

The graph E was formed by using a current of 30 mA flowing in an LED in a light emitting element, which is a normal value, as a one parameter, and the graph F was formed by using a current of 70 mA flowing in an LED in a light emitting element, which is a maximum value, as another parameter. The portion C of each graph indicates that the data of this portion was taken in a normal way and, therefore, the transmitted light value was increased because the lubricating oil could not pass entirely through the space, and the portion D of each graph indicates that data of this portion was taken in such a manner that the lubricating oil was previously filled in the space manually because the space was too narrow to allow the lubricating oil to pass through the space in the normal way.

Figure 14:
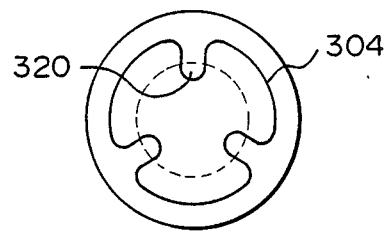
FIG. 14 is a plane view of a spacer used in the detecting device in FIG. 13.
Figure 15:
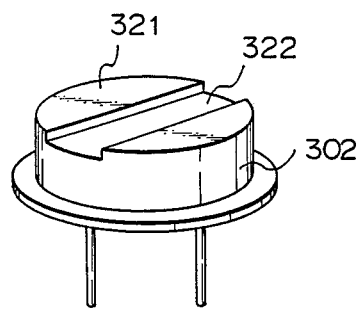
FIG. 15 is a perspective view of another embodiment of a spacer used in this invention.
Figure 16:
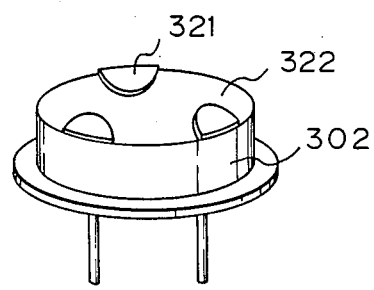
FIG. 16 is a perspective view of another embodiment of a spacer used in this invention; and, FIG. 17 is a graph indicating a relationship between a distance of a space provided between the light emitting element and the photo detecting element, and a current output by a photo detecting element and corresponding to a detected light transmitted through a substance.

The embodiments of a configuration of a spacer 304 used in this invention are shown in FIGS. 14 to 16.

In particular, in FIG. 14, a spacer 304 having a ring-like configuration with a plurality of projections 320 projected into the inside of the ring from an internal edge thereof is explained, and a dotted line representing an external border line of a light emitting element 301, i.e., a diameter thereof, is added to this Figure.

In this invention, a spacer can be made of any material as long as the object of the invention is attained, but a transparent material is most preferable because there an advantage is gained in that the amount of light to be detected by a photo detecting element (SPD) can be increased.

In FIGS. 15 and 16, spacers having several projections 321 which define at least one groove or channel 322 for a substance to pass therethrough are explained. In this embodiment, such a projection of a groove is provided directly on the photo detecting element, and in FIG. 15, the groove 322 is provided by cutting the surface of the element. On the other hand, in FIG. 16, the projecting portion 321 is provided by using materials selected from an organic component, for example, a fluorine polymer, and an inorganic component such as a metal or ceramic, by a process of coating, vacuum evaporation, and adhesion.

As mentioned above, the spacer of this invention is not necessarily separated from such an element but may be provided on any one of the elements, and when a photo detecting element provided with projecting portions on the surface thereof is used, the amount of the detected light value can be increased because the transmittal of the light is not disturbed by the spacer.

A light emitted from the light emitting element is usually transmitted to the photo detecting element in a diverged condition and, therefore, preferably the photo detecting element has a diameter larger than that of the light emitting element, to enable a more efficient detection of the light emitted from the light emitting element.

According to the device having the construction as shown above, the space between those elements can be maintained at a constant distance by utilizing a spring force, even when portions of the device are deformed by thermal expansion or thermal shrinkage or the like caused by a thermal transmission of the heat from the engine, reducing the space to be varied.

In this invention, the oscillating circuit mentioned above may be incorporated into the unit with the light emitting element, and further, the photo detecting element may be also incorporated into the unit. According to this invention, the light emitting element and the photodetecting element are incorporated into a unit form such as a small brick or the like, and further, the photodetecting element and the photosocillating circuit are incorporated into a unit form, whereby a solid photodetecting device having a small size and a high reliability can be obtained.

The device of this invention outputs a digital signal, not an analog signal, from an oscillator which is not affected by temperature, and therefore, the signal output from the oscillator can be transmitted to a display means remote from the detecting circuit without noise.

Further, the device of this invention can maintain an accurate operation even when provided on a portion having a high temperature, for detecting contamination, for example.

According to this invention, to overcome the temperature drawbacks of the device, this invention was based upon a concept such that a contamination of, for example, a fluid does not develop so rapidly, and in relation to an internal combustion engine provided on a vehicle, the degree of contamination can be discriminated by measuring the lubricating oil once at every operation of the vehicle, and further, although elements used in an electronic circuit usually have an operating temperature of about 80° C. as an upper limit thereof, because of a self heating thereof or the like, it can bear up to 150° C. as a storage temperature when a power is cut off.

Therefore, in this invention, the device for detecting the degree of contamination for example, is further provided with a temperature detecting circuit. Accordingly, when the temperature of a substance, for example, a fluid, becomes high, a power supply to the detecting device including a light emitting element and a photo detecting element affected by such a high temperature is cut OFF by an output signal from the temperature detecting circuit and, accordingly, an accurate measurement of a degree of contamination of a fluid can be made because the storage temperature of each element exceeds the maximum temperature of 145° C. of the lubricating oil and the elements are protected from damage caused by a high temperature.

In this invention, instead of using such a temperature detecting circuit, a counter circuit which can control the detecting and discriminating operation in such a way that the timer counter outputs a signal to start the detecting and discriminating operation to detect the certain transmissivity, and a signal to stop the operation before the temperature of, for example, the oil, reaches a predetermined temperature, or outputs a signal to start the operation after the temperature of the oil reaches the predetermined temperature and outputs a signal to stop the operation before the temperature reaches an upper limit of the temperature, beyond which the light emitting element and a photo detecting element can not work efficiently, may be used.

Next, another embodiment of a device of this invention including all of the features mentioned above and a discriminating circuit for discriminating a transmissivity including a degree of contamination of a substance will be explained.

The fifth embodiment of the detecting device of this invention, also intended to be used in particular for detecting a degree of contamination of a lubricating oil of an internal combustion engine, will be explained.

Figures 10, 10A:
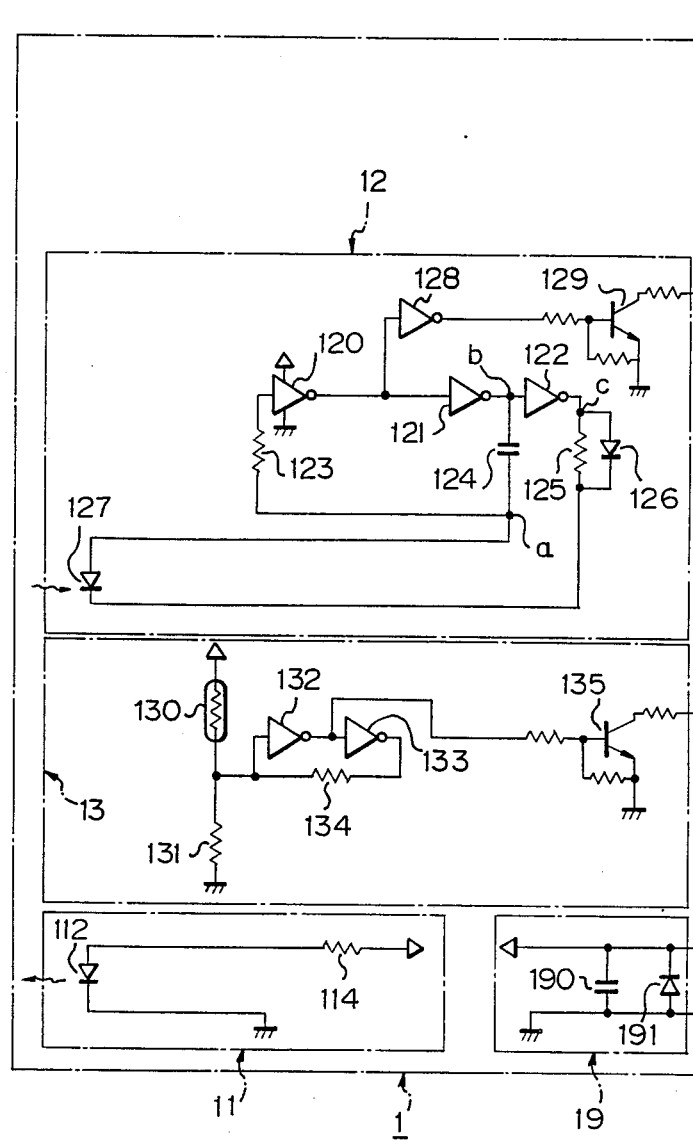
FIG. 10 shows an electric circuit of the fifth embodiment of a device of the invention.
Figure 10B:
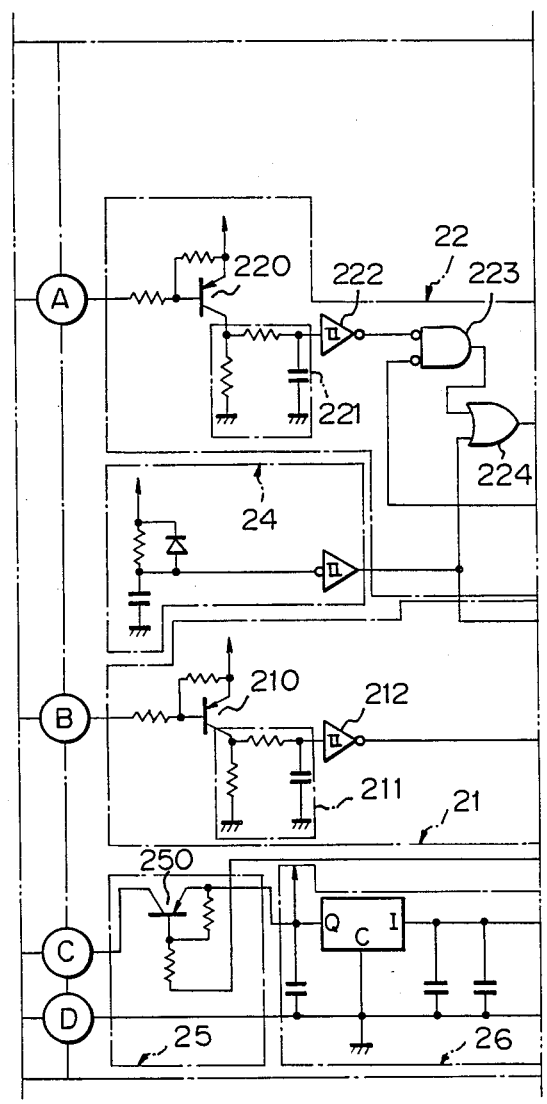
Figure 10:
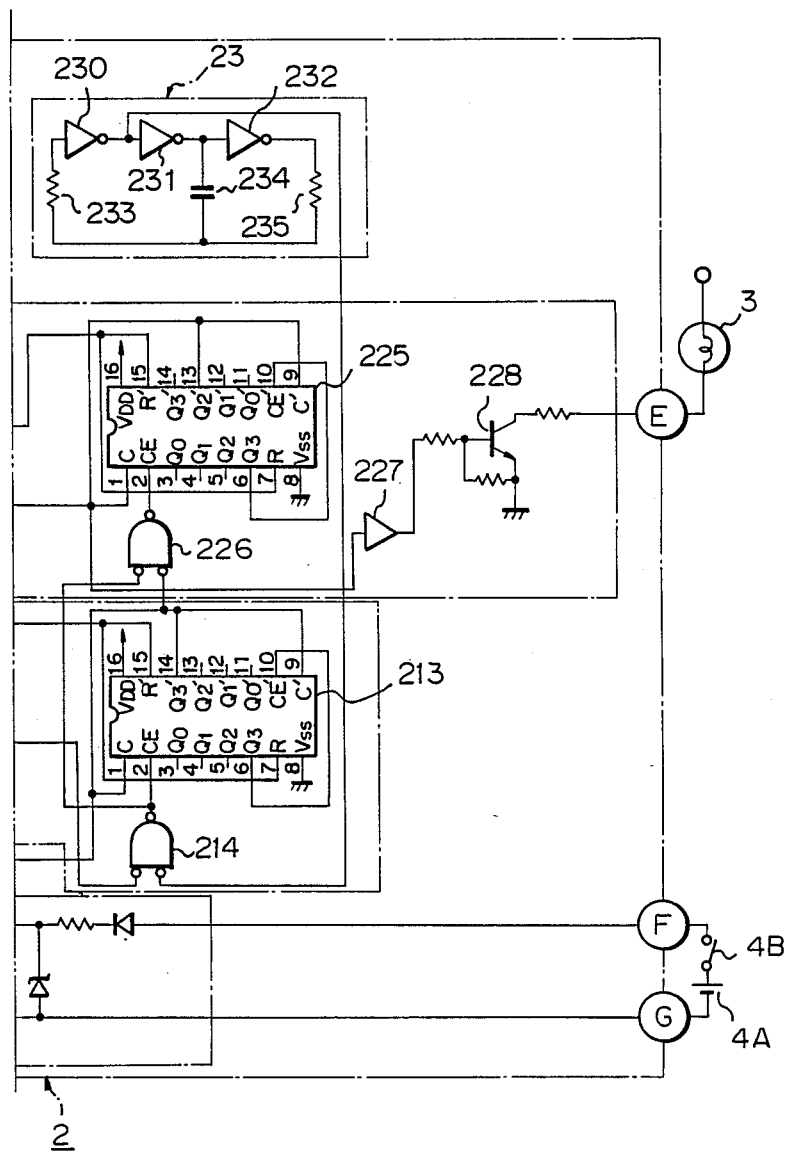

FIG. 10 shows an electric circuit used in the fifth embodiment.

In this FIG. 10, a detecting circuit 1 comprises a light emitting circuit 11 and a photo detecting and photo oscillating circuit 12, both of which have the same electronic circuit and components as described in FIG. 1, and therefore, each component in FIG. 10 corresponding to each component in FIG. 1 is given the same number as in FIG. 1 and suffixed by the number 100.

The output of the photo detecting and photo oscillating circuit 12 is taken out from an open collector of a transistor 129 through an output terminal of an inverter 120 and inverter 128 as a buffer.

In the detecting circuit 1, a temperature detecting circuit 13 is also provided in which a variation of a temperature is converted into a variation of a voltage by a positive characteristic thermistor 130 and a dividing resistor 131, and the resultant voltage is output from a transistor 135 as a signal for a temperature, through a comparator circuit with hysteresis comprising inverters 132 and 133 and a feedback resistor 134.

A power supply circuit 19 comprises a protecting diode 191 and a smoothing condensor 190.

Figure 11:
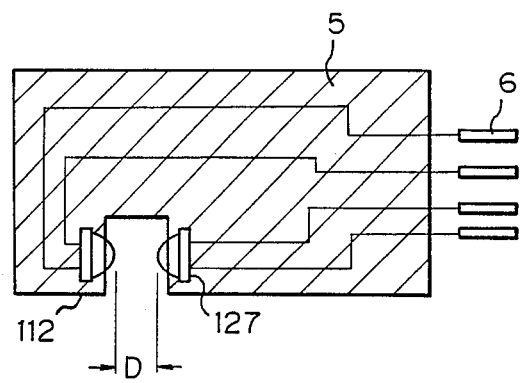
FIG. 11 is a cross sectional view of a detector indicating an arrangement of a light emitting element and a photo detecting element used in the circuit of FIG. 10.

In the detecting circuit of the device of this invention, the LED 112 and the SPD 127 are fixedly arranged face to face in a body 5 which is immersed in the lubricating oil as a fluid to be measured, with a small space D therebetween as shown in FIG. 11, and signals are output and input through a terminal 6 respectively.

On the other hand, the thermistor 130 is mounted on an outer surface of an internal combustion engine for detecting a temperature of the lubricating oil, and other elements are mounted on an outer surface of an internal combustion engine in such a way that the connecting line connecting the elements to the LED 112 and the SPD 127 in this circuit is made as short as possible.

A discriminating circuit 2 comprises a timing circuit 21, a counting circuit 22, a reference signal generating circuit 23, a power reset circuit 24, a power control circuit 25, and a power stabilizing circuit 26.

In the timing circuit 21, an output signal of the temperature detecting circuit 13 in the detecting circuit 1 is input to a transistor 210 through a terminal B, and an output thereof is input to a CE terminal of timing generating counter IC 213 (for example, TOSHIBA TC4520BP) through a Schmidt trigger circuit IC 212 (for example, TOSHIBA TC4584BP) and a gate 214, after filtering pulse noise in a CR filter 211.

In a counting circuit 22, an output signal of a photo detecting and photo oscillating circuit 12 of a detecting circuit 1 is input to a transistor 220 through a terminal A, and an output thereof is input to an R terminal of a counting IC 225 (for example, TOSHIBA TC4520BP) through a Schmidt trigger circuit IC 222, gates IC 223 and 224, after filtering pulse noise in a CR filter 221.

An output from a terminal Q2' of the IC 225 is taken out as an output from an open collector of a transistor 228 through a buffer IC 227.

In a reference signal generating circuit 23, a reference oscillating signal is generated by an astable multivibrator comprising CMOS inverters 230, 231, and 232, resistors 233 and 235, and a condensor 234.

A power reset circuit 24 outputs a reset signal when an electric power is supplied.

In a power control circuit 25, a transistor 250 serves as an ON-OFF control of the supply of an electric power to the detecting circuit 1 corresponding to the detected temperature of the lubricating oil through terminals C and D corresponding to an input signal from the timing circuit 21.

A power stabilizing circuit 26 converts a voltage input from an external direct current source 4A through a switch 4B and terminals F and G into a stable voltage, for example, +5 V, and supplies the voltage to each of the above circuits.

A warning lamp 3 provides a warning of a condition of a contamination in the fluid detected by receiving a signal from the counting circuit 22 through a terminal E.

Next, the operation of each circuit of the device of this embodiment is explained.

The operation of the photo detecting and photo oscillating circuit 12 is the same as that of the circuit shown in FIG. 1.

Next, with regard to the operation of the temperature detecting circuit 13, a positive characteristic thermistor 130 has a characteristic such that the value of a resistance is low when a temperature is low, and vice versa, and therefore, the output of the inverter 132 can be made "L" level when the temperature is lower than a predetermined value and "H" level when the temperature is higher than a predetermined value, by adjusting a value of the thermistor 130 and the dividing resistor 131 to make the divided potential between the thermistor 130 and the dividing resistor 131 a threshold voltage of the inverter 132 at the predetermined temperature.

An inverter 133 and a feedback resistor 134 are further provided for eliminating chatter of the output of the inverter 132 by adding an hysteresis to the input threshold voltage of the inverter 132.

The operation of the counting circuit 2 is now explained.

First, when electric power is supplied from an external power source, the power stabilizing circuit 26 is actuated and a stabilized voltage is supplied to each circuit.

The power resetting circuit 24 outputs a reset single having an "H" level pulse after when a stabilized voltage is supplied thereto and directly resets the counter 213 to the initial condition and sets the counter 225 to the initial condition through the gate 224.

In this condition, the transistor 250 of the power controlling circuit 25 is made ON because the output terminal Q3' of the counter 213 is "L" level, and thus the stabilized voltage is also supplied to the detecting circuit 1.

At this time, a temperature of a lubricating oil of an internal combustion engine is low and, therefore, an output of the inverter 132 is "L" level, and accordingly, the transistor 135 is OFF.

Therefore, as the output of the transistor 210 is also OFF and the output of the inverter 212 is "H" level, the output of the gate 214 is "H" level.

Further, the output of the gate 214 is simultaneously input to the gate 226, and therefore, the output of the gate 226 is "H" level, and thus the reference oscillating signal of the reference signal generating circuit 23 is not input to the counter 213 and 225 and these counters are not actuated.

When a temperature of the lubricating oil rises to a predetermined temperature, (the temperature is set at one degree lower than an upper limit of the operating temperature of any element used; in this embodiment the temperature is set at 60° C., for example) both the transistors 135 and 210 are turned ON, and thus the output of the inverter 212 is made "L" level.

Accordingly, the reference oscillating signal of the reference signal generating circuit 23 is output at each output terminal of the gates 214 and 226, and thus a count up of both counters 213 and 225 is begun by the reference oscillating signal.

On the other hand, the output of the photo detecting and photo oscillating circuit 12 of the detecting circuit 1, is input to the terminals R and R' of the counter 225 through the gates 223 and 224.

The waveform of the input voltage at the terminal is the same as shown in FIG. 2(b) in this situation, and the smaller the amount of light detected by the photo detecting element, i.e., the higher the degree of contamination, the longer the duration for which the voltage is "L" level.

The duration for which the input voltage to the input terminals R and R' is "L" level is shorter than the time interval in which a predetermined number of reference oscillating signals are counted up by the counter, for example, for a time needed to count up 64 pulses, the output of the terminal Q2' is not made "H" level, but when the degree of contamination goes beyond a predetermined level, the output of the terminal Q2' is made "H" level, accordingly.

When the output of the terminal Q2' is made "H" level, the output terminals C and C' of the counter 225 are also made "H" level, which prevents the count up operation thereof and, simultaneously, the input signal to one of the input terminals of the gate 223 is made "H" level, and the output of the gate 223 is made "L", and thus the signal having the "H" level cannot be input to the terminals R and R' of the counter 225.

The "H" level signal output from the terminal Q2' causes the warning lamp 3 to be turned ON through the buffer 227 and the transistor 228.

On the other hand, the counter 213, which starts counting up simultaneously with the counter 225, makes the output of the terminal Q3' "H" level after the counter 213 has counted up a predetermined number of the reference oscillating signals, for example, 128, which prevents the counter 213 from counting up, and finally, the input of the reference oscillating signals to the counter 225 is stopped by the gate 226.

Namely, at this time, the output level of the terminal Q2' of the counter 225 is held and the output signal having the "H" level at the terminal Q3' of the counter 213 makes the transistor 225 of the power control circuit 25 OFF, and thus the supply of a stabilized voltage to the detecting circuit 1 is stopped.

Accordingly, the device in accordance with the invention described above starts the discrimination of the degree of contamination after the electric power is supplied and the temperature of a lubricating oil reaches a predetermined temperature lower than the upper limit of an operative temperature of each element used, and when the degree of contamination exceeds a predetermined value, the warning lamp is turned ON.

The detecting circuit 1 is the inactivated after a predetermined time has passed, assuming that the temperature of the oil will go beyond such an upper limit later.

If the predetermined value for the degree of contamination for turning the warning lamp ON must be changed, it may be carried out by varying the cycle of the reference oscillating signals by changing the value of the resistance 235 of the reference oscillating circuit 23 or by varying the intensity of the LED 112 of the light emitting circuit 11 by changing the value of the current control resistance 114.

The sixth embodiment of the device of this invention will now be described.

Figure 12:
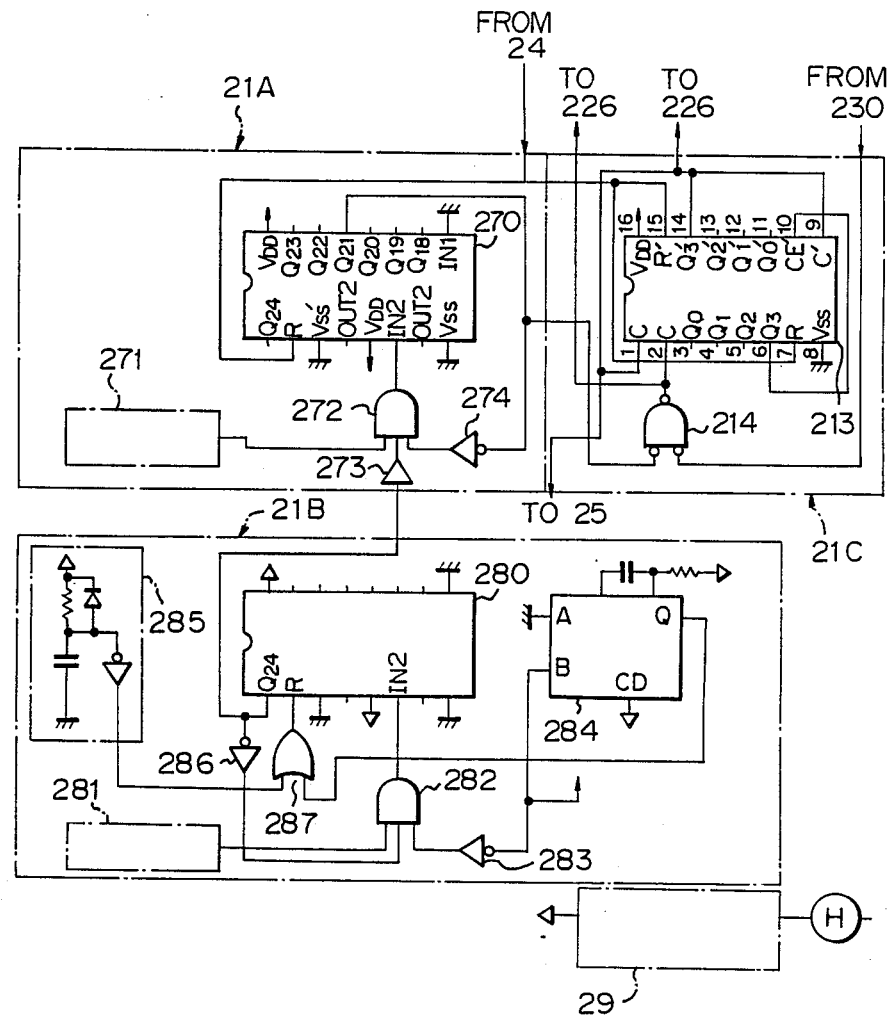
FIG. 12 shows a portion of an electric circuit of the sixth embodiment of a device of the invention.

This embodiment has a configuration such that the temperature detecting circuit 13 is eliminated from the circuit of the fifth embodiment shown in FIG. 10, and the timing circuit 21 is modified to the circuit as shown in FIG. 12.

In FIG. 12, a first timer circuit 21A comprises a counter IC 270 (for example, TOSHIBA TC4521BP) an oscillating circuit 271 (i.e., the same circuit as the reference signal generating circuit 23 in FIG. 10), a gate 272, a level converting buffer 273, and an inverter 274, and a second timer circuit 21B comprises a counter IC 280 (the same as 270), an oscillating circuit 281 (the same as 271), gates 282 and 287, inverters 283 and 268, a one shot astable multivibrator 284 (for example, TOSHIBA TC4528BP), and a power reset circuit 285 (i.e., the same as the circuit 24 in FIG. 10).

A second power stabilizing circuit 29 is provided for generating a stabilized voltage of +5 V and supplying same to the second timer circuit 21B.

The operation of the embodiment mentioned above will now be explained.

When an electric power from an external direct current source is first supplied to this circuit, the second power stabilizing circuit 29 is first actuated and then the second timer circuit is actuated.

The counter 280 is reset to an initial condition by the power reset circuit 285.

Assuming that the external direct current source is controlled to be supplied to the power stabilizing circuit 26 in FIG. 10 through the switch 4B only when the internal combustion engine is operating, when the internal combustion engine is not operating, the input of the inverter 283 to which the electric power is supplied is "L" level, and thus the counter 280 starts the counting-up with the clock signal input thereto from the oscillating circuit 281 through the gate 282.

After a predetermined time has passed (for example, 40 minutes), the output of the output terminal Q24 is made "H" level and the counter stops the count up because the gate 282 is made OFF.

Next, when the operation of the internal combustion engine is started, the power stabilizing circuit 26 starts to supply electric power to all of the circuits.

In the first timer circuit, when the input of the gate 273, i.e., the output at the terminal Q24 of the second timer, is "H" level, the count-up by the counter 270 is started by the clock signal input thereto from the oscillating circuit 271 through the gate 272, and after a predetermined time has passed (for example, 5 minutes), the output of the terminal Q21 is made "H" level.

This output signal is used as an input signal to the gate 214 in the discriminating circuit 21C, and thereafter, the discriminating operation is started in the same manner as described for the fifth embodiment.

When, the operation of the internal combustion engine is stopped, the counter 280 is reset by the pulse output from the terminal Q caused by the conversion from "H" level to "L" level of the input signal to the terminal B of the one shot astable multivibrator 284 in the second timer circuit.

Briefly, in the sixth embodiment, the discriminating operation is carried out in such a way that, as the temperature of the lubricating oil of an internal combustion engine is proportional to the time of operation of the engine, the engine operation is first started when the temperature of the lubricating oil has sufficiently dropped after a predetermined time has passed since the engine has stopped operation, and then the degree of contamination is measured after a predetermined time has passed from when the engine started operation.

After the predetermined time has passed, the detecting circuit is deactivated as in the fifth embodiment.

In this embodiment, the degree of contamination is discriminated after the temperature of, for example, the oil, has reached a predetermined level or after a predetermined time has passed since the engine started operation, and then the detecting circuit is deactivated. The discrimination of the degree of contamination may be carried out continuously when the temperature reaches the predetermined temperature and the detecting circuit may be deactivated after the temperature has reached the predetermined value or after the predetermined time has passed since the engine started operation. Further, the predetermined temperature may be set at approximately the upper limit of the operative temperature of any of the elements used in the circuit, and the detecting circuit may be actuated only when the measuring operation is carried out, so as to extend the life of the LED and reduce the power consumption.

Further, in these embodiments, to discriminate the degree of contamination, the duration of the cycle of the output signal from the detecting circuit is utilized, but instead, the discriminating operation may be carried out by utilizing a level of the frequency, and the number of discrimination operations is not restricted to only one time but may be carried out depending upon the average value based upon a plurality of the data measured.

In these embodiments, as a display of the degree of contamination measured, only the degree of contamination having a level exceeding a predetermined value is displayed. However, a plurality of such measurements can be made and the results displayed simultaneously in a form of a bar-graph or the like, or the level of contamination may be measured as continuous data and displayed in digital form or the like.

Moreover, in the fifth embodiment, a positive characteristic thermistor is used for detecting the temperature of the lubricating oil, but another thermodetection element, for example, a negative characteristic thermistor, may be used, and further, a sensor for detecting the temperature of a cooling water of an internal combustion engine also may be used as an extra measure.

As described above, according to this invention, a transmissivity of a substance, based upon for example, a quality or a degree contamination, is detected by detecting a transmitted light value by using a photo oscillator circuit as a photo detecting means comprising a photo detecting element detecting a light emitted from a light emitting element and transmitted through the substance.

Therefore, accurate data on a condition or a degree of contamination of a substance can be detected by using a circuit having a simple configuration and by utilizing output signals having a cycle or a frequency with strong antinoise characteristics.

Further, as described above, when a detecting device having a light emitting element and a photo detecting means which is immersed in a fluid, for example, a lubricating oil, is placed directly or indirectly in such a position that the temperature thereof is at a predetermined high temperature, an electric power supply is stopped and, therefore, the light emitting element and photo detecting element are protected from the effect of the heat even when a temperature of a substance, for example, a gas or fluid, is raised, thereby allowing the detecting device of this invention to reliably detect and discriminate a degree of contamination of the substance.

Moreover, in this invention, the device is little affected by variations in temperature, and thus is able to maintain an accurate operation even in a high temperature environment, and further, can transmit an output signal unaffected by noise to a display means remote from the detector. Further, by using the device according to this invention, a detecting and discriminating operation of a transmissivity of a substance can be carried out accurately by adopting a suitable spacial distance and a diameter of the light emitting element and photo detecting element, respectively.

We claim:

1. A device formed in a housing portion for detecting a transmissivity of a substance, comprising:
   light emitting means including a light emitting element; and
   photodetecting means including a photodetecting element, said photodetecting means being spaced from said light emitting means by a predetermined distance, said photodetecting means for detecting a transmitted light value of a substance passing through a space between said light emitting means and said photodetecting means as an amount of light transmitted through said substance, said photodetecting means comprising a photooscillator circuit including said photodetecting element as one component element thereof for outputting a signal having characteristics selected from a cycle and a frequency corresponding to said transmitted light value, said photodetecting means being incorporated with said photodetecting element as a unit which is fixedly provided inside a housing portion of said device.

2. A device for detecting a transmissivity of a substance according to claim 1, wherein said substance is a fluid.

3. A device for detecting a transmissivity of a substance according to claim 2, wherein the transmissivity to be detected of said substance is a degree of contamination thereof.

4. A device for detecting a transmissivity of a substance according to claim 1, further comprising a spacer between the light emitting means including the light emitting element and the photodetecting means including the photodetecting element and photooscillating circuit, and wherein said device further comprises a cover having at least one opening allowing a substance to be passed therethrough, said light emitting means and said photodetecting means provided inside the cover and spaced at a predetermined width from each other by said spacer provided therebetween, said space between said light emitting means and said photodetecting means communicating with the opening of the cover, at least one housing provided inside the cover for supporting the light emitting means and the photodetecting means and a spring provided inside of the cover to ensure a firm contact between the light emitting means and the photodetecting means.

5. A device for detecting a transmissivity of a substance according to claim 1, wherein a diameter of the light emitting element is smaller than a diameter of the photodetecting element.

6. A device for detecting a degree of contamination of a fluid according to claim 3, wherein said light emitting element and said photodetecting element are provided in a lubricating oil of an internal combustion engine.

7. A device for detecting a degree of contamination of a fluid according to claim 6, wherein said space between said light emitting element and said photodetecting element is between 40 μm and 170 μm.

8. A device for detecting a transmissivity of a substance according to claim 1, wherein said photooscillator circuit is an astable multivibrator outputting a signal having characteristics selected from a cycle and a frequency corresponding to a duration in which said photodetecting element has a reverse bias varying in accordance with an amount of light detected by said photodetecting element.

9. A device for detecting a transmissivity of a substance according to claim 8, wherein said astable multivibrator comprises a plurality of inverters connected in series and a series circuit including a resistor, a photodetecting element and a capacitor.

10. A device for detecting a transmissivity of a lubricating oil of an internal combustion engine, comprising:
detecting means, having a light emitting means and a photodetecting means, both of which are immersed in said lubricating oil to be measured, and operating from an electric power, for detecting a light transmitted by said light emitting means through said oil by said photodetecting means and producing a signal indicative thereof;
discriminating means for discriminating a transmitted light value based upon the signal from the detecting means and an electric power supplied to said detecting means when said detecting means is in condition that the temperature thereof is higher than a predetermined temperature;
wherein said detecting means includes means for detecting a condition of said lubricating oil by starting operation when supplying an electric power to the detecting means and subsequently stopping the power supply thereto depending upon a time of operation of the engine, and making a determination based on the temperature of the oil increasing to a predetermined temperature after a predetermined time has passed since the engine is started.

11. A device for detecting a transmissivity of a substance according to claim 10, wherein the detecting means comprises a photooscillator circuit having an oscillator cycle thereof which varies in correspondence to an amount of light detected by the photodetecting element, for outputting a signal having a cycle corresponding to a transmitted light value of said lubricating oil.

12. A device for detecting a transmissivity of a substance, comprising:
a light emitting circuit including a light emitting element and a photodetecting circuit including a photodetecting element, spaced from each other by a predetermined distance, for detecting a transmitted light value of a substance passing through a space between said light emitting element and said photodetecting circuit as a transmitted light value, a photooscillator circuit including said photodetecting element as one component element thereof which outputs a signal having characteristics selected from a cycle and a frequency corresponding to said transmitted light value, a temperature detecting circuit outputting a signal when the substance has a temperature exceeding a predetermined temperature, a discriminating circuit for discriminating the condition of the substance detected by the signal output from the photooscillator circuit and comprising a reference signal generating circuit, a counting circuit for counting clock pulses, a power circuit supplying a power to said temperature detecting circuit, a timing circuit, a count of which is started by a clock pulse of the output signal of said reference signal generating circuit, and which passes the clock pulse to said counting circuit when the output signal of said temperature detecting circuit is input and which stops the counting operation and outputs a signal for cutting off said power circuit supplying a power to said temperature detecting circuit when a predetermined number of pulses are counted by said counting circuit, the count of said counting circuit is started when a clock pulse from the count circuit is input thereto, and the output signal of the photooscillator circuit is input to a reset terminal thereof, and when a predetermined number of the clock pulses are counted up before a reset signal is input thereto from said oscillator circuit, the count thereof is stopped and a signal for actuating a warning lamp circuit is output.

13. A device for detecting a transmissivity of a substance, comprising a light emitting circuit including a light emitting element, a photodetecting circuit including a photodetecting element, each of which are spaced from each other by a predetermined distance so that a transmitted light value of a substance passing through a space between said photodetecting element and said light emitting element is detected as a transmitted light value, a photooscillator circuit including said photodetecting element as one component element thereof which outputs a signal having characteristic s selected from a cycle and a frequency corresponding to said transmitted light value, a detecting operation controlling circuit comprising a first timer circuit which begins to count reference signals after a signal corresponding to a startup signal of an engine is input to the reset terminal thereof, and outputs a signal for stopping the counting operation thereof when a output signal of a second timer is input thereto, and for starting the discriminating operation of a discriminating circuit, after a predetermined number of pulses are counted, and a second timer circuit which starts to count up reference signals when power is supplied thereto and outputs a signal for stopping the count thereof and for starting the count of the first timer after a predetermined number of pulses are counted and is reset when a signal corresponding to an engine stop is input to a reset terminal thereof, a discriminating circuit for discriminating the condition of the substance detected by the signal output from the photooscillator circuit comprising a reference signal generating circuit, a timing circuit, the count of which is started by a clock pulse of the output signal of said reference signal generating circuit and which passes the clock pulse to a count circuit when the output signal of said temperature detecting circuit is input thereto and stops the count and outputs a signal for cutting off a power circuit supplying power to said temperature detecting circuit when a predetermined number of pulses are counted up, a counting circuit the count of which is started when the clock pulse from the count circuit is input thereto, and the output signal of the photooscillator circuit is input to a reset terminal thereof, and when a predetermined number of the clock pulses are counted before a resetting signal is input thereto from said oscillator circuit, the count thereof is stopped and a signal for actuating a warning lamp circuit is output.

* * * * *